(12) United States Patent
Tseng et al.

(10) Patent No.: US 9,354,250 B1
(45) Date of Patent: May 31, 2016

(54) NANOSCALE PROBE STRUCTURE AND APPLICATION THEREOF

(71) Applicant: National Tsing Hua University, Hsinchu (TW)

(72) Inventors: Fan-Gang Tseng, Hsinchu (TW); Yi-Chuan Chen, Hsinchu (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 0 days.

(21) Appl. No.: 14/671,235

(22) Filed: Mar. 27, 2015

(30) Foreign Application Priority Data

Nov. 14, 2014 (TW) .............................. 103139625 A

(51) Int. Cl.
*G01Q 70/16* (2010.01)
*G01Q 70/14* (2010.01)
*C12Q 1/42* (2006.01)

(52) U.S. Cl.
CPC ........ *G01Q 70/14* (2013.01); *C12Q 1/42* (2013.01); *C12Y 306/01001* (2013.01)

(58) Field of Classification Search
CPC ..... G01Q 70/14; C12Q 1/42; C12Y 306/01001
USPC .............................. 850/56, 57, 60, 61, 62, 63
See application file for complete search history.

(56) References Cited

U.S. PATENT DOCUMENTS

2009/0134025 A1\* 5/2009 Shtein .................... B82Y 35/00 204/407

OTHER PUBLICATIONS

Tuhin Subhra Santra et al., "Impact of pulse duration on localized single-cell nano-electroporation", Analyst, 2014, 139, pp. 6249-6258.

\* cited by examiner

*Primary Examiner* — Michael Maskell
(74) *Attorney, Agent, or Firm* — WPAT, P.C. Intellectual Property Attorneys; Anthony King

(57) ABSTRACT

A nanoscale probe structure, including: a first probe having a tip top end and a second probe having a planar top end, wherein a metallic layer coats the on the tip top end, an insulating layer coats around the tip top end of the first probe; and a metallic layer coats on the planar top end, an insulating layer coats around the planar top end of the second probe. The structure of present invention can applied in atomic force microscopy to measure the electricity physiology signal inside and outside the cell membrane, which can limit the measure region to specific little area for the measure of electricity physiology signal and effectively decrease the miscellaneous noise disturbance from other region.

14 Claims, 9 Drawing Sheets

NANOSCALE PROBE STRUCTURE AND APPLICATION THEREOF

CROSS-REFERENCE TO RELATED APPLICATION

This application claims the priority of Taiwanese patent application No. 103139625, filed on 14 Nov. 2014, which is incorporated herewith by reference.

BACKGROUND OF THE INVENTION

1. Field of the Invention

The invention relates to a probe structure, more particularly, the invention also relates to a nanoscale probe structure.

2. The Prior Arts

The researchers have concerned the issue about what is the role of cell membrane in the membrane for a long time. It is a barrier between inside and outside of the cell to form a closed system. In addition, the ion flowing in the cell membrane is an interesting biological phenomenon, organism generates energy in respiration and photosynthesis system by obtaining a ion current, the ion current can change the characteristics of the organism, comprising: changing chemical molecules, the osmotic pressure, and ion balance in the biological body which produces different potential difference for organisms to use in active transport and cell migration.

On the other hand, it relies on the cell membrane proton pump to keep the pH value constant, the proton pump can control proton to pass in and out the cell membrane, so as to generate a proton gradient between the extracellular and cytoplasmic sides. It needs energy supply for membrane protein to transport substance passing in and out the cell membrane, the energy supply is nothing more than active transport pump (such as $H^+$-ATPase) or proton gradient. Moreover, it also can transport substance to pass in and out the cell membrane by exchange of substance. These mechanisms of these transports are used to keep ion constant in the cytoplasm and metabolic regulation in organism, therefore, pH gradient in cytoplasm can be an important driving force in the organism to transport nutrient into the cell from external environment, the difference of pH gradient in cytoplasm and tiny organelle supplies energy to most of the secondary transmission system, which makes more substance entry the cell membrane. Thus, the domestic and foreign scholars have deeply concerned about the structure and reaction mechanism of the membrane protein, as well as its proton transfer coupled reaction for a long time, the scholars all hope to further research.

Atomic Force Microscopy (AFM) is a nanoscale scanning probe microscopes with high resolution, a cantilever probe with tapered tip measures across a surface and collects the signal, which is mainly used to measure the precise shape of the test sample, and accuracy of the measurement result significantly correlates with the geometry shape and size of the probes. However, current AFM technique cannot measure a reaction mechanism of individual molecule in cell membrane, but a wide range of measurement will lead to excessive noise and interference, it cannot completely show the electrophysiological signals inside and outside of the cell membrane. What is needed is a platform of measuring electrophysiological signals used as a good model of researching a coupled mechanism between "enzyme reaction" and "transporting hydrogen ions", which also can be used to research and analyze the regulation mechanism on the cell membrane for pathological mechanism and drug screening of a disease related to a nervous system, muscular system and cardiovascular system.

SUMMARY OF THE INVENTION

To solve the problem, the present invention provides a nanoscale probe structure, comprising: a first probe having a tip top end; and a second probe having a planar top end, wherein the tip top end is coated with a metallic layer, and the first probe is coated with an insulating layer around the tip top end; and the planar top end is coated with a metallic layer, the planar top end is coated with an insulating layer around the planar top end; and wherein the metallic layer on the first probe or the second probe is a platinum (Pt) metallic layer or a iridium (Ir) metallic layer.

In one embodiment, the insulating layer on the first probe is a hafnium oxide ($HfO_2$) insulating layer, and the insulating layer on the second probe is a hafnium oxide ($HfO_2$) insulating layer.

In one embodiment, the tip top end area of the first probe is in the range of 500 $nm^2$ to 2,500 $nm^2$.

In one embodiment, the planar top end area of the second probe is in the range of 0.25 $\mu m^2$ to 1 $\mu m^2$.

In one embodiment, the thickness of the metallic layer of the first probe and the second probe are in the range of 15 nm to 50 nm.

In one embodiment, the thickness of the insulating layer of the first probe and the second probe are in the range of 10 nm to 30 nm.

In one embodiment, the planar top end is used to carry a micro-droplet.

The present invention also provides a detector of measuring an electrophysiological signal on membrane channel proteins, comprising: a first probe having a tip top end; a second probe having a planar top end, wherein the tip top end is coated with a metallic layer, and the first probe is coated with a hafnium oxide ($HfO_2$) insulating layer around the tip top end; the planar top end is coated with a metallic layer, and the second probe is coated with a hafnium oxide ($HfO_2$) insulating layer around the planar top end; and wherein the metallic layer on the first probe or the second probe is a platinum (Pt) metallic layer or a iridium (Ir) metallic layer.

In one embodiment, the first probe and the second probe are atomic force microscopy (AFM) probes.

In one embodiment, the planar top end carries a micro-droplet having a liposome, and the tip top end enters into the liposome, and the detector measures an electrophysiological signal on membrane channel proteins embedded in the liposome via the tip top end and the planar top end closing to each other.

The present invention still provides a method of measuring an electrophysiological signal on membrane channel proteins, comprising: providing a first probe having a tip top end, wherein the tip top end is coated with a metallic layer, and the first probe is coated with a hafnium oxide ($HfO_2$) insulating layer around the tip top end; providing a second probe having a planar top end, wherein the planar top end is coated with a metallic layer, and the second probe is coated with a hafnium oxide ($HfO_2$) insulating layer around the planar top end; loading a micro-droplet having a liposome on the planar top end; entering the tip top end into the liposome; and closing the tip top end and the planar top end to each other to measure an electrophysiological signal on membrane channel proteins embedded in the liposome, wherein the metallic layer on the first probe or the second probe is a platinum (Pt) metallic layer or a iridium (Ir) metallic layer.

In one embodiment, the first probe and the second probe are atomic force microscopy (AFM) probes.

The detailed technology and above preferred embodiments implemented for the present invention are described in the following paragraphs accompanying the appended drawings for people skilled in this field to well appreciate the features of the claimed invention.

DETAILED DESCRIPTION OF THE PREFERRED EMBODIMENT

The present invention provides a nanoscale probe structure, which uses a pairs of probes as the two end of the detector, the upper probe is sequentially coated with a platinum (Pt) metallic layer and a hafnium oxide ($HfO_2$) insulating layer, and the tip top end can be modified to expose the platinum metallic layer; the lower probe is also sequentially coated with a platinum (Pt) metallic layer and a hafnium oxide ($HfO_2$) insulating layer, and blunting the tip top end. The nanoscale probe structure of the present invention can be the nano-electrode to measure the electrophysiological signal for the structure of a membrane protein and a reaction mechanism.

Figure 1:
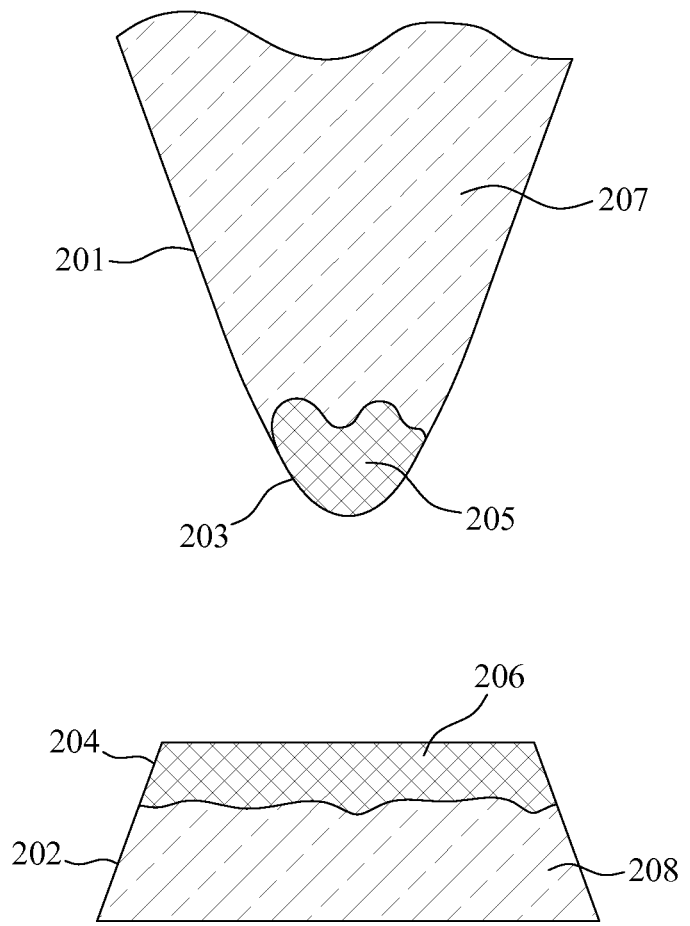
FIG. 1 is a view shows a nanoscale probe structure of the present invention.

To provide a further understanding the feature of the present invention, as shown in FIG. 1, the nanoscale probe structure of the present invention, comprising: a first probe 201 having a tip top end 203; and a second probe 202 having a planar top end 204, wherein the tip top end 203 is coated with a metallic layer 205, and the first probe 201 is coated with an insulating layer 207 around the tip top end 203; and the planar top end 204 is coated with a metallic layer 206, and the second probe 202 is coated with an insulating layer 208 around the planar top end 204.

Figure 2:
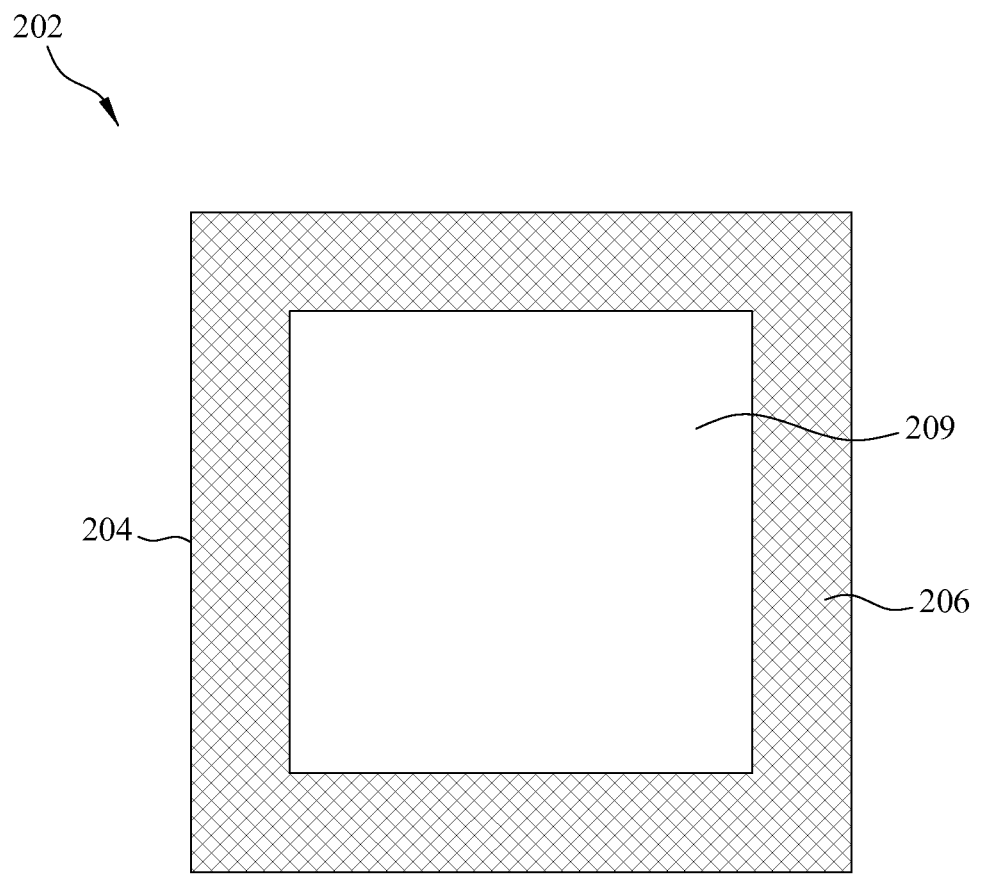
FIG. 2 shows a top view of the planar top end of the second probe of the nanoscale probe structure in the present invention.

In addition, FIG. 2 shows a top view of the planar top end 204 of the second probe 202 of the nanoscale probe structure in the present invention, the planar top end 204 of the second probe 202 exposes a few parts of the metallic layer 206 and foloading flat 209.

The present invention also provides a detector of measuring an electrophysiological signal on membrane channel proteins, comprising an atomic force microscopy (AFM) having a nanoscale probe structure as shown in FIG. 1, wherein the planar top end 204 of the second probe 202 carries a microdroplet having a liposome, and the tip top end 203 of the first probe 201 enters into the liposome to measure an electrophysiological signal on membrane channel proteins embedded in the liposome via the a pair of first probe 201 and the second probe 202 of the atomic force microscopy closing to each other.

EXAMPLE 1

Preparation of the Nanoscale Probe of the Present Invention

Figure 3:
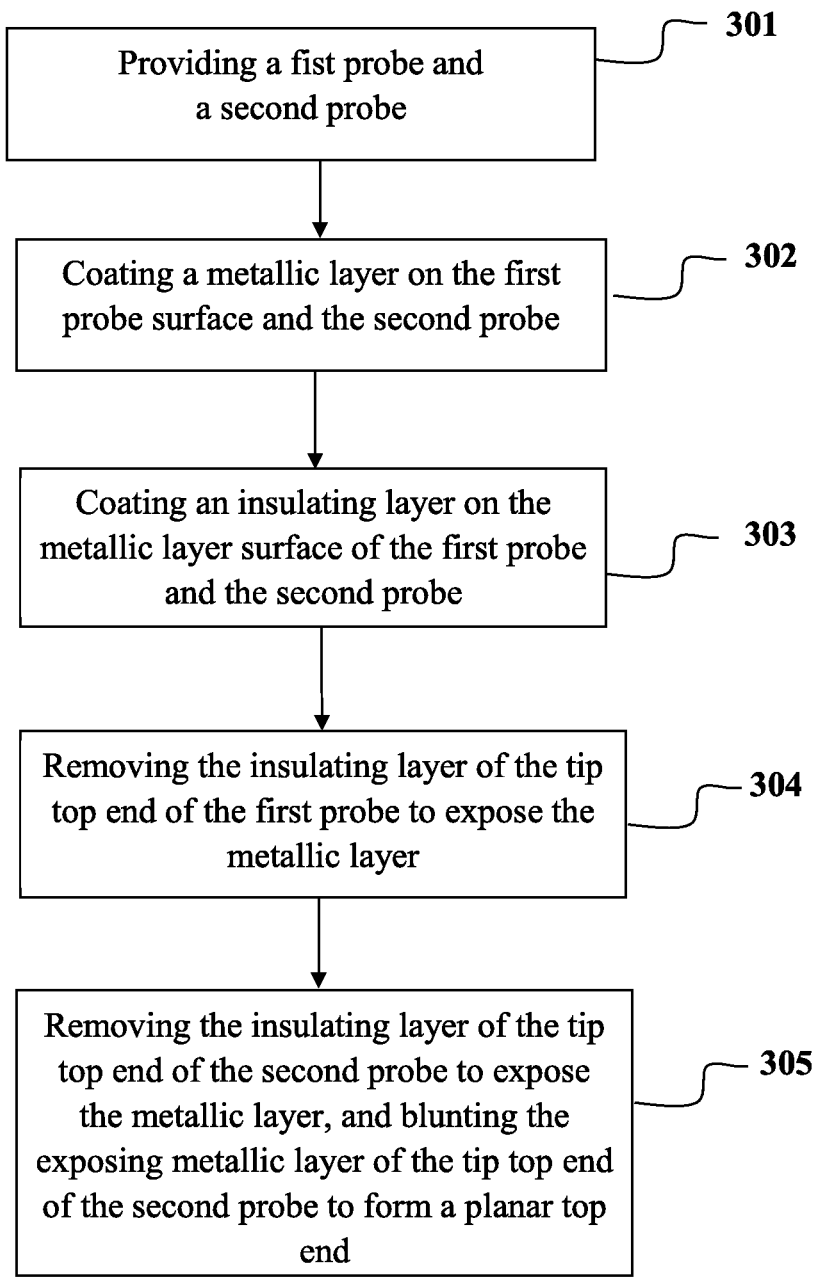
FIG. 3 shows a flowchart of the steps for manufacturing a nanoscale probe structure according to a preferred embodiment of the present invention.
Figure 4A:
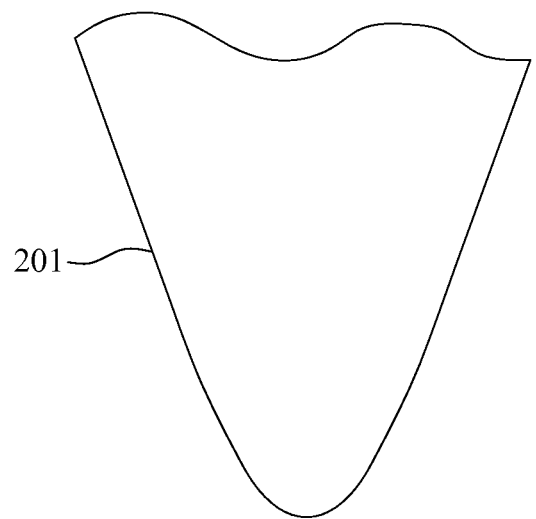
FIGS. 4A to E show the method of manufacturing a nanoscale probe structure according to a preferred embodiment of the present invention.
Figure 4A:
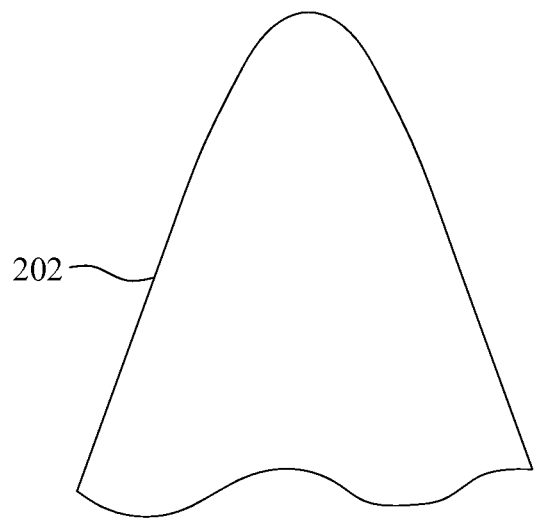
Figure 4B:
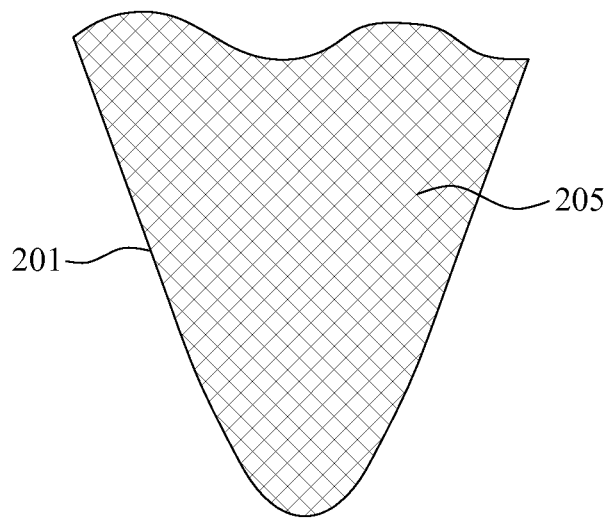
Figure 4B:
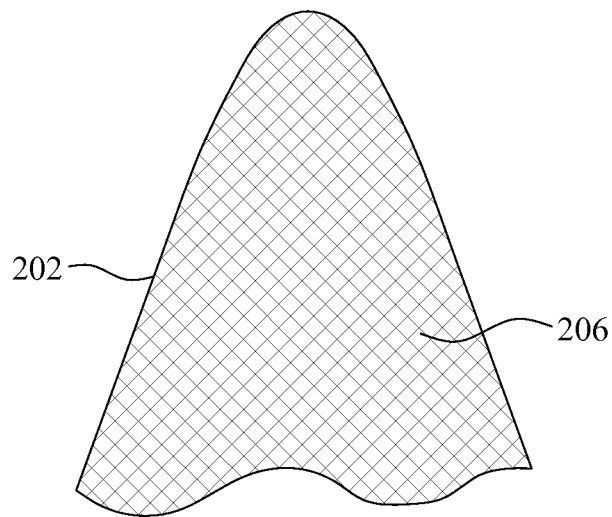
Figure 4C:
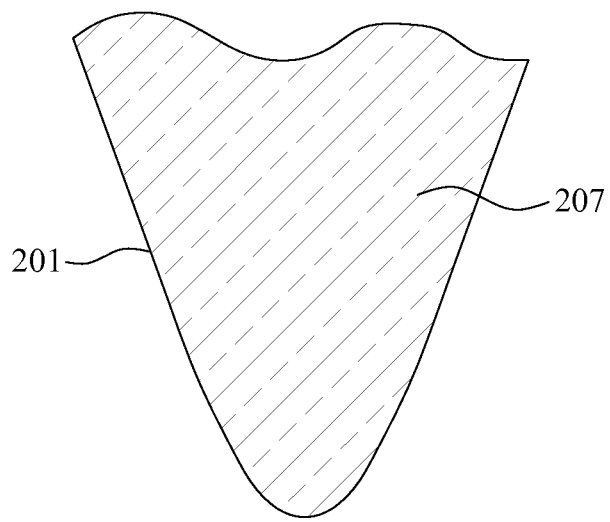
Figure 4C:
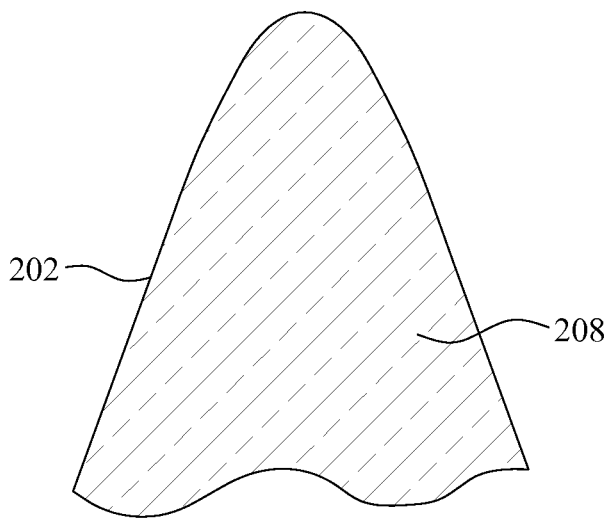
Figure 4D:
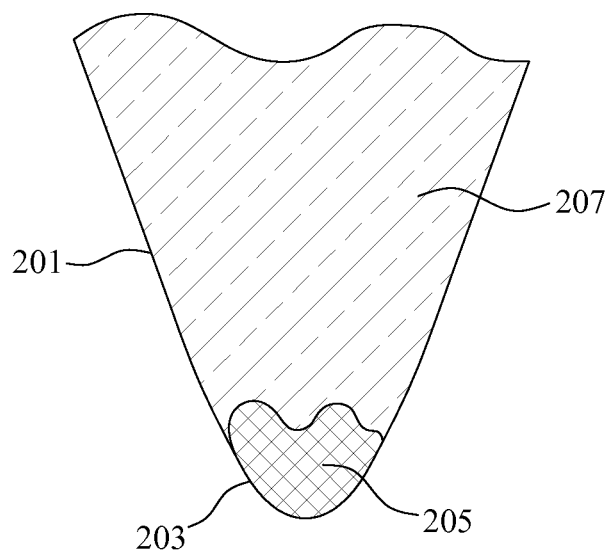
Figure 4D:
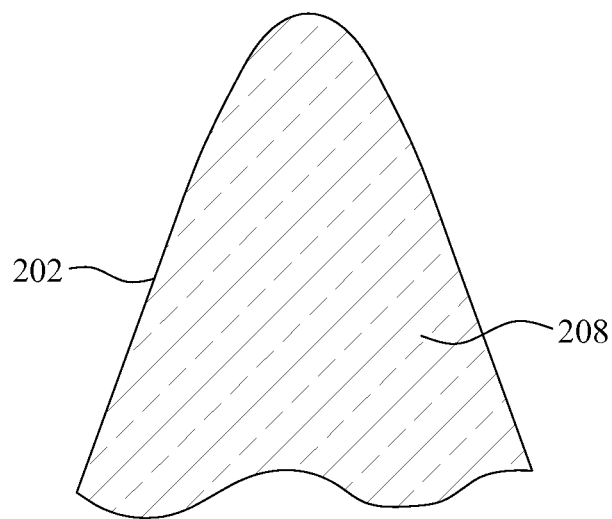
Figure 4E:
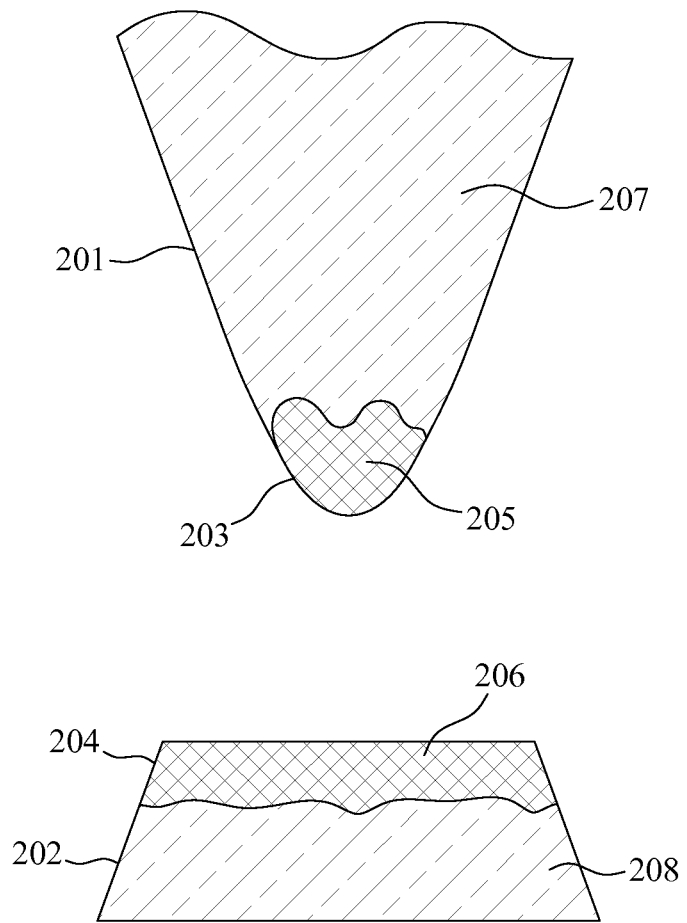

FIG. 3 illustrates with reference to FIGS. 4 A to E. First, step 301 in FIG. 3 illustrates with reference to FIG. 4 A, providing a first probe 201 and a second probe 202; follow by step 302 in FIG. 3 illustrating with reference to FIG. 4 B, coating a metallic layer 205 on the surface of the first probe 201, and coating a metallic layer 206 on the surface of the second probe 202, wherein the metallic layer 205 and 206 are preferably platinum (Pt) metallic layers or iridium (Ir) metallic layers; follow by step 303 illustrating with reference to FIG. 4 C, depositing an insulating layer 207 on the metallic layer 205 surface of the first probe 201 by using atomic layer deposition, and depositing an insulating layer 208 on the metallic layer 206 surface of the second probe 202, wherein the insulating layer 207 and 208 are preferably silicon dioxide ($SiO_2$) insulating layers or hafnium oxide ($HfO_2$) insulating layers; follows by step 304 illustrating with reference to FIG. 4 D, removing the insulating layer 207 on the tip top end 203 of the first probe 201 to expose a few part of the metallic layer 205; finally, follows by step 305 illustrating with reference to FIG. 4 E, removing the insulating layer 208 on the tip top end of the second probe 202 to expose a few part of the metallic layer 206, blunting the exposing metallic layer 206 on the tip top end of the second probe 202 to form a planar top end 204 having a larger area than exposing the metallic layer area of the first probe 201 (upper probe). Connecting the terminal ends of the first probe 201 and the second probe 202 to a current supply conductor connected with a power supply and an oscilloscope.

In one embodiment of the present invention, the metallic layer 205 and 206 are platinum (Pt) metallic layers or iridium (Ir) metallic layers.

In one embodiment of the present invention, the insulating layer 207 and 208 are silicon dioxide ($SiO_2$) insulating layers or hafnium oxide ($HfO_2$) insulating layers.

In one embodiment of the present invention, the metallic layer 205 of the first probe 201 and the metallic layer 206 of the second probe 202 may be the same or not, and the insulating layer 207 of the first probe 201 and the insulating layer 208 of the second probe 202 may be the same or not.

In one embodiment of the present invention, the tip top end 203 area of the first probe 201 is in the range of 500 $nm^2$ to 2,500 $nm^2$, and the planar top end 204 area of the second probe 202 is in the range of 0.25 $\mu m^2$ to 1 $\mu m^2$.

In one embodiment of the present invention, the thickness of the metallic layer 205 and 206 is in the range of 15 nm to 50 nm.

In one embodiment of the present invention, the thickness of the insulating layer 207 and 208 is in the range of 10 nm to 30 nm.

EXAMPLE 2

Application of the Nanoscale Probe of the Present Invention

In the present invention, the liposome having the membrane channel proteins is applied to a system of measuring electrophysiological signal, wherein the method of manufacturing the liposome having the membrane channel proteins is not limited. In one embodiment, take 1 to 200 nm liposome to the buffer containing 20 mM MOPS-KH (pH7.0), 80 mM KCl, 1 mM MgSO$_4$ and 10% glycerol and following detection of the liposome.

Both the nano-electrodes in the present invention use the standard potential of silver-silver chloride electrode, which having the advantage of non-polarized characteristics is widely applied in patch clamp electrophysiology techniques. To measure the electrical current passing between two electrodes in a cell while a voltage is applied, the silver-silver chloride electrode is not because of applying voltage to change the balance potential, therefore, it can reduce the current measurement errors. Such electrode must have basic requirement, that is, the solution for measurement must contain chloride ion (Cl$^-$), the reversible reaction is Ag$^+$+Cl$^-$→AgCl+e$^-$. Currently, the thin silver wire can be coated with silver chloride uniformly to insert into the potassium chloride (KCl) droplet through the upper and lower surface. The charge and discharge signal generated in the process of bilayer membranes formation is measured by oscilloscope to calculate the capacitance value of the lipid bilayer membranes.

Figure 5:
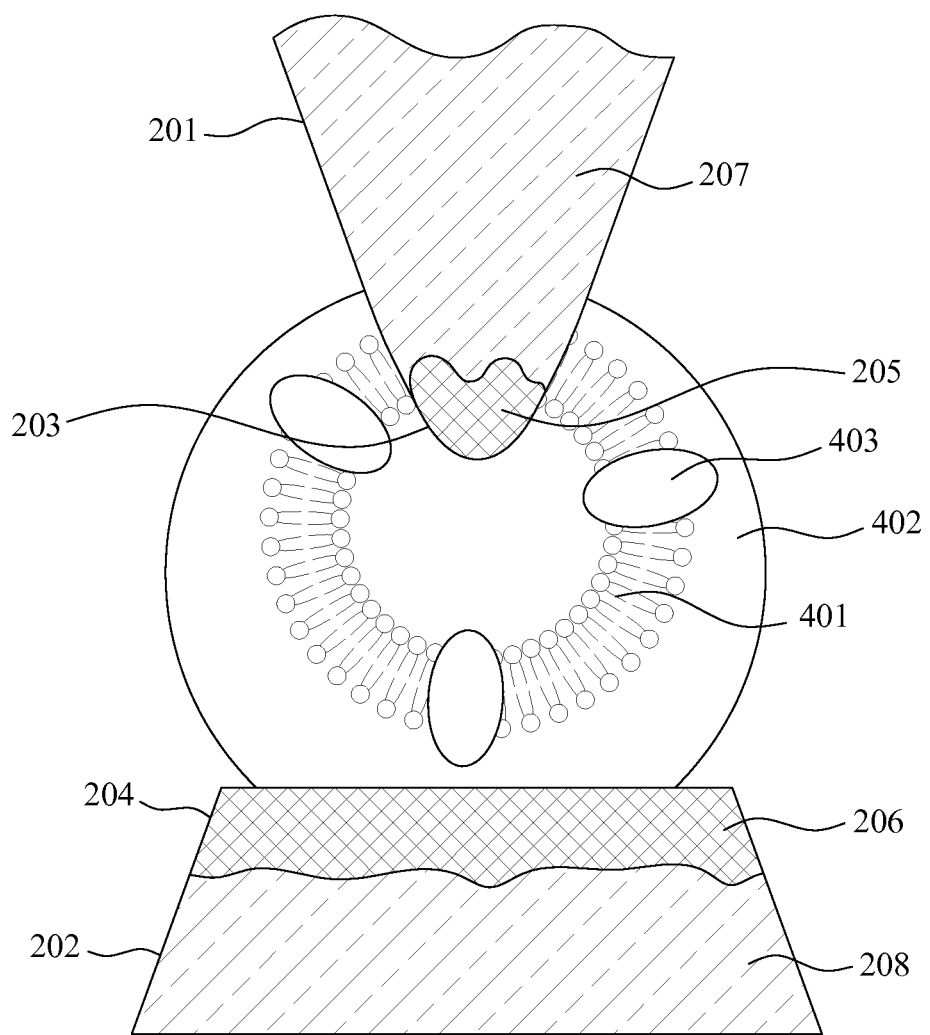
FIG. 5 shows that the nanoscale probe structure of the present invention is applied in the membrane channel proteins of a liposome.

After the lipid bilayer formation, scanning the surface of the lipid bilayer membranes by an atomic force microscopy to obtain the distribution location of the liposome having the membrane channel proteins. As shown in FIG. 5, the atomic force microscopy (AFM) having a nanoscale probe structure of the present invention is used to measure the liposome 401 having the membrane channel proteins 403 in the droplet 402, liposome 401 is loaded on the lower probe (second probe 202), and the upper probe (first probe 201) enters into the liposome 401. Applying a current signal from outside, the signal is from the exposing the nano-metallic layer of the tip top end 203 of the upper probe (first probe 201) through transmembrane channel in the membrane channel proteins 403 formed by liposome 401 molecules to be absorbed by the planar top end 204 of the lower probe (second probe 202), which forms a current path.

Therefore, the nanoscale probe structure of the present invention is to coat a metallic layer on the surface of the atomic force microscopy probe, and deposit an insulating layer, then remove the insulating layer on the tip top end of the probe exposing a few part of the probe. Connecting the terminal ends of the probes to a current supply conductor connected with a power supply and an oscilloscope. The nanoscale probe structure can be probe-type nano-electrode to measure nano current signal at initial electrochemical measurement.

EXAMPLE 3

Construct the Model of Proton-Pumping Pyrophosphatase (H$^+$-PPase) in Proton-Pumping Channel and Dynamic Analysis In the past, there is a great finding in some pathogenic bacteria cells and corps through the detection of proton-pumping pyrophosphatase (H$^+$-PPase), it is extremely important to understand the function of the enzyme in the proton transfer channel structure for physiological treatment, but there is still no found in the human body.

The nanoscale probe structure of the present invention is applied to observing the location of dynamic reaction of the single molecular proton-pumping pyrophosphatase (H$^+$-PPase) in hydrogen ion pumping channel of the artificial lipid bilayer membrane. Measure the electrophysiology signal of around single membrane protein in the artificial lipid bilayer membrane by reconstructing single protein in the artificial lipid bilayer membrane, fluorescence resonance energy transfer, current detection techniques and the nanoscale probe structure of the present invention.

Since the membrane protein reconstructed in the artificial lipid bilayer membrane is still active. When hydrogen ions are transported, hydrogen ions are closer to the pumping channel, the higher concentration it will be, otherwise the concentration is lower. Therefore, the nanoscale probe of the present invention can scan the single protein in the artificial lipid bilayer membrane, and detect the concentration of the hydrogen ions, the location of dynamic reaction, rate and power parameters in the pumping channel.

Since the nanoscale probe structure of the present invention is applied to solving the traditional bottleneck in location and structure of the protein transport channel, and it can be combined with structural analysis techniques, such as X-ray, to analyze the location and structure of the protein transport channel so as to construct this model. One preferred embodiment of the present invention is helpful to realize dynamic physiological reaction, the structure of hydrogen ion transport channel and titer of transporting hydrogen ion in a single membrane protein (e.g. H$^+$-PPase). In addition, the nanoscale probe structure of the present invention is also applied to other types of an ion channel, a protein channel, a water channel and a nerve conduction channel, etc.; it can be used for location and analysis the protein transport channel.

In summary, the present invention provides a nanoscale probe structure used for the atomic force microscopy as the electrical signal measurement electrodes, which can develop a platform of electrophysiological signal measurement. The platform can measure the electrophysiological signal in local area for lipid bilayer membrane location, which can clearly scan the location of the protein in the membrane, narrow down the range to specific small area when measuring the electrophysiological signal inside and outside of the cell membrane, and effectively minimize noise interference in other regions to measure the signal in local area.

What is claimed is:

1. A nanoscale probe structure, comprising:
 a first probe having a tip top end; and
 a second probe having a planar top end,
 wherein the tip top end is coated with a metallic layer, and the first probe is coated with an insulating layer around the tip top end;
 the planar top end is coated with a metallic layer, and the planar top end is coated with an insulating layer around the planar top end; and
 wherein the metallic layer on the first probe or the second probe is a platinum (Pt) metallic layer or a iridium (Ir) metallic layer.

2. The nanoscale probe structure according to claim 1, wherein the insulating layer on the first probe is a hafnium oxide (HfO$_2$) insulating layer.

3. The nanoscale probe structure according to claim 1, wherein the insulating layer on the second probe is a hafnium oxide (HfO$_2$) insulating layer.

4. The nanoscale probe structure according to claim 1, wherein the tip top end area of the first probe is in the range of 500 nm$^2$ to 2,500 nm$^2$.

5. The nanoscale probe structure according to claim 1, wherein the planar top end area of the second probe is in the range of 0.25 μm$^2$ to 1 μm$^2$.

6. The nanoscale probe structure according to claim 1, wherein the thickness of the metallic layer of the first probe and the second probe are in the range of 15 nm to 50 nm.

7. The nanoscale probe structure according to claim 1, wherein the thickness of the insulating layer of the first probe and the second probe are in the range of 10 nm to 30 nm.

8. The nanoscale probe structure according to claim 1, wherein the planar top end is used to carry a micro-droplet.

9. A detector of measuring an electrophysiological signal on membrane channel proteins, comprising:
   a first probe having a tip top end; and
   a second probe having a planar top end,
   wherein the tip top end is coated with a metallic layer, and the first probe is coated with a hafnium oxide ($HfO_2$) insulating layer around the tip top end;
   the planar top end is coated with a metallic layer, and the second probe is coated with a hafnium oxide ($HfO_2$) insulating layer around the planar top end; and
   wherein the metallic layer on the first probe or the second probe is a platinum (Pt) metallic layer or a iridium (Ir) metallic layer.

10. The detector according to claim 9, wherein the first probe and the second probe are atomic force microscopy (AFM) probes.

11. The detector according to claim 9, wherein the planar top end carries a micro-droplet having a liposome, and the tip top end enters into the liposome.

12. The detector according to claim 11, wherein the detector measures an electrophysiological signal on membrane channel proteins embedded in the liposome via the tip top end and the planar top end closing to each other.

13. A method of measuring an electrophysiological signal on membrane channel proteins, comprising:
   providing a first probe having a tip top end, wherein the tip top end is coated with a metallic layer, and the first probe is coated with a hafnium oxide ($HfO_2$) insulating layer around the tip top end;
   providing a second probe having a planar top end, wherein the planar top end is coated with a metallic layer, and the second probe is coated with a hafnium oxide ($HfO_2$) insulating layer around the planar top end;
   loading a micro-droplet having a liposome on the planar top end;
   entering the tip top end into the liposome; and
   closing the tip top end and the planar top end to each other to measure an electrophysiological signal on membrane channel proteins embedded in the liposome,
   wherein the metallic layer on the first probe or the second probe is a platinum (Pt) metallic layer or a iridium (Ir) metallic layer.

14. The method according to claim 13, wherein the first probe and the second probe are atomic force microscopy (AFM) probes.

* * * * *